United States Patent [19]

Minai et al.

[11] Patent Number: 4,535,182
[45] Date of Patent: * Aug. 13, 1985

[54] PROCESS FOR PREPARING 2-CYCLOPENTENONE ESTERS

[75] Inventors: Masayoshi Minai, Moriyama; Tadashi Katsura, Osaka, both of Japan

[73] Assignee: Sumitomo Chemical Company, Limited, Osaka, Japan

[*] Notice: The portion of the term of this patent subsequent to Jan. 29, 2002 has been disclaimed.

[21] Appl. No.: 523,602

[22] Filed: Aug. 16, 1983

[30] Foreign Application Priority Data

Aug. 26, 1982 [JP] Japan .................. 57-148609
Aug. 27, 1982 [JP] Japan .................. 57-149450
Nov. 12, 1982 [JP] Japan .................. 57-199588

[51] Int. Cl.³ .............................. C07C 69/02
[52] U.S. Cl. .................. 560/231; 560/254; 560/255; 560/256
[58] Field of Search .......... 560/231, 254, 255, 256

[56] References Cited

U.S. PATENT DOCUMENTS 4,347,386  8/1982  Saito et al. .................. 568/341
4,371,711  2/1983  Saito et al. .................. 568/341

Primary Examiner—Paul J. Killos
Attorney, Agent, or Firm—Birch, Stewart, Kolasch & Birch

[57] ABSTRACT

2-Cyclopentenone esters of the formula:

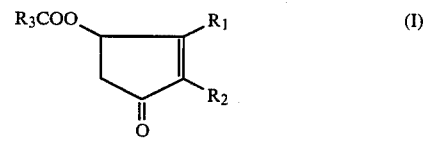

wherein $R^1$ is hydrogen, lower alkyl or lower alkenyl, $R^2$ is lower alkyl, lower alkenyl, lower alkynyl, or cycloalkyl, cycloalkenyl or substituted or unsubstituted aryl and $R^3$ is hydrogen or lower alkyl are prepared in high yields by reacting the corresponding racemic or optically active 4-cyclopentenone of the formula:

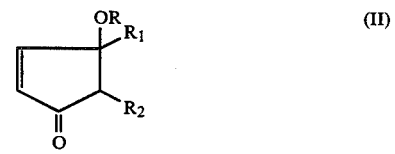

wherein $R^1$ and $R^2$ are each as defined above and $R^3$ is hydrogen or acyl with at least one lower aliphatic carboxylic acid and/or metal or amine salts thereof.

9 Claims, No Drawings

PROCESS FOR PREPARING 2-CYCLOPENTENONE ESTERS

The present invention relates to a process for preparing 2-cyclopentenone esters. More particularly, it relates to a process for preparing 2-cyclopentenone esters of the formula:

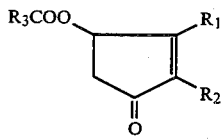

wherein $R_1$ is hydrogen, lower alkyl or lower alkenyl, $R_2$ is lower alkyl, lower alkenyl, lower alkynyl, cycloalkyl, cycloalkenyl or substituted or unsubstituted aryl and $R_3$ is hydrogen or lower alkyl.

In the above significances, the term "lower" is intended to mean a group having not more than 8 carbon atoms. Thus, examples of lower alkyl are methyl, ethyl, n-propyl, isopropyl, n-butyl, isobutyl, n-pentyl, n-hexyl, n-heptyl, etc.; examples of lower alkenyl are allyl, 1-methylallyl, 1-ethylallyl, 4-pentenyl, 2,4-pentadienyl, 2-cis-butenyl, 2-cis-pentenyl, 2-trans-pentenyl, etc.; examples of lower alkynyl are ethynyl, 2-propynyl (namely propargyl), 2-pentynyl, etc. The term "aryl" is intended to mean an aromatic group having not more than 18 carbon atoms, and its examples are phenyl, naphthyl, anthryl, etc. A substituent which is optionally present on the aryl group may be lower alkyl, lower alkoxy, halogen. etc. The terms "cycloalkyl" and "cycloalkenyl" are intended to mean groups having not more than 12 carbon atoms, and examples thereof include cyclopropyl, cyclopentyl, cyclohexyl, cyclopentenyl, cyclohexenyl, etc.

The 2-cyclopentenone esters (I) are per se useful as agricultural chemicals and also as intermediates in the production of agricultural chemicals, medicines and perfumes. For example, they can be reduced with the combination of zinc powder and acetic acid to give substances which are extremely useful as perfumes.

The 2-cyclopentenone esters (I) have been prepared by esterification of the corresponding alcohols or by substitution of the halogen atom at the 4-position on the 2-cyclopentenone ring with an acyloxy group, these conversions being representable by the following formulas:

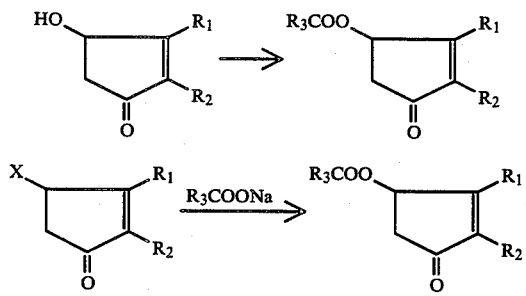

wherein $R_1$, $R_2$ and $R_3$ are each as defined above and X is a halogen atom (e.g. chlorine, bromine).

However, these conventional procedures are not satisfactory from the industrial veiwpoint, since they require expensive starting materials.

There is also known a process for preparing 4-acetoxy-2-phenyl-2-cyclopentenone by adsorbing 3-acetoxy-2-phenyl-4-cyclopentenone on 30 times its weight of alumina (Tetrahedron, Vol. 35, 135 (1979)), the conversion being representable by the formulas:

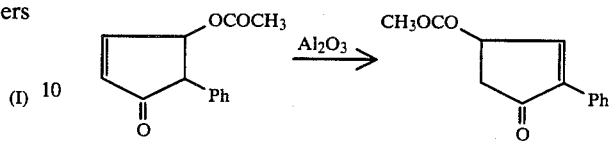

This process is not an industrially preferred process, since a large amount of alumina should be used. In addition, the application of this process to the corresponding alkyl, alkenyl, alkynyl, cycloalkyl or cycloalkenyl analogue at the 2-position gives the desired product only in a very low yield.

As a result of an extensive study, the adoption of an entirely novel reaction has succeeded in production of the 2-cyclopentenone esters (I) in high yields.

According to the present invention, the 2-cyclopentenone ester (I) can be prepared by reacting the corresponding racemic or optically active 3-hydroxy or acyloxy-4-cyclopentenone of the formula:

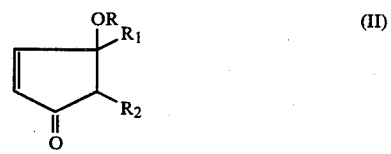

wherein $R_1$ and $R_2$ are each as defined above and R is hydrogen or acyl such as formyl or lower alkanoyl with at least one of the lower aliphatic carboxylic acids and their metal and amine salts.

The starting 4-cyclopentenone (II) can be produced, for example, by rearrangement of the corresponding furan-carbinol, optionally followed by esterification as shown in the following scheme:

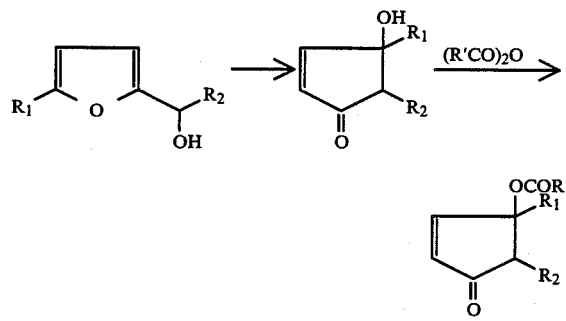

wherein $R_1$ and $R_2$ are each as defined above and R' is hydrogen or acyl such as formyl or lower alkanoyl.

Specific examples of the 4-cyclopentenone (II) are 3-hydroxy-2-methyl-4-cyclopentenone, 3-hydroxy-2-ethyl-4-cyclopentenone, 3-hydroxy-2-n-propyl-4-cyclopentenone, 3-hydroxy-2-isopropyl-4-cyclopentenone, 3-hydroxy-2-n-butyl-4-cyclopentenone, 3hydroxy-2-n-pentyl-4-cyclopentenone, 3-hydroxy-2-n-hexyl-4-cyclopentenone, 3-hydroxy-2-n-heptyl-4-cyclopentenone, 3-hydroxy-2-allyl-4-cylopentenone, 3-hydroxy-2-(2-cis-butenyl)-4-cyclopentenone, 3-hydroxy-2-(ω-butenyl)-4-cyclopentenone, 3-hydroxy-2-(2-trans-pentenyl)-4-cyclopentenone, 3-hydroxy-2-(3- cis-hexenyl)-4-cyclopentenone, 3-hydroxy-2-(2-cis-pentenyl)-4-cyclopentenone, 3-hydroxy-2-propargyl-4-cyclopentenone, 3-hydroxy-2-(2-pentynyl)-4-cyclopentenone, 3-hydroxy-2-(α-methylallyl)-4-cyclopentenone, 3-hydroxy-2-(1-cyclopentenyl)-4-cyclopentenone, 3-hydroxy-2-cyclohexyl-4cyclopentenone, 3-hydroxy-2,3-dimethyl-4-cyclopentenone, 3-hydroxy-2-ethyl-3-methyl-4-cyclopentenone, 3-hydroxy-2-n-propyl-3-methyl-4-cyclopentenone, 3-hydroxy-2-isopropyl-3-methyl-4-cyclopentenone, 3-hydroxy-2-n-butyl-3-methyl-4-cyclopentenone, 3-hydroxy-2-n-pentyl-3-methyl-4-cyclopentenone, 3-hydroxy-2-n-hexyl-3-methyl-4-cyclopentenone, 3-hydroxy-2-n-heptyl-3-methyl-4-cyclopentenone, 3-hydroxy-2allyl-3-methyl-4-cyclopentenone, 3-hydroxy-2-(2-cis-butenyl)-3-methyl-4-cyclopentenone, 3-hydroxy-2-(ω-butenyl)-3-methyl-4-cyclopentenone, 3-hydroxy-2-(2-cis-pentenyl)-3-methyl-4-cyclopentenone, 3-hydroxy-2-(2-trans-pentenyl)-3-methyl-4-cyclopentenone, 3-hydroxy-2-(3-cis-hexenyl)-3-methyl-4-cyclopentenone, 3-hydroxy-2-propargyl-3-methyl-4-cyclopentenone, 3-hydroxy-2-(2-pentynyl)-3-methyl-4-cyclopentenone, 3-hydroxy-2-(α-methylallyl)-3-methyl-4-cyclopentenone, 3-hydroxy-2-(1-cyclopentenyl)-3-methyl-4-cyclopentenone, 3-hydroxy-2-cyclohexyl-3-methyl-4-cyclopentenone, 3-hydroxy-2-phenyl-3-methyl-4-cyclopentenone, 3-hydroxy-2-(p-chlorophenyl)-3-methyl-4-cyclopentenone, etc. Their corresponding 3-acyloxy derivatives such as 3-acetoxy or 3-propionyloxy derivatives are also usable. Further, these compounds may be racemic or optically active.

Specific examples of the lower aliphatic carboxylic acid are formic acid, acetic acid, propionic acid, butyric acid, valeric acid, etc. As their metal salts, there are exemplified a lithium salt, sodium salt, potassium salt, calcium salt, copper salt, zinc salt, palladium salt, lead salt, tin salt, manganese salt, etc. As their amine salts, there are exemplified a trimethylamine salt, triethylamine salt, pyridine salt, picoline salt, etc. Their mixtures are also usable, and preferred is the combined use of the lower aliphatic carboxylic acid and its metal salt.

The reaction between the 4-cyclopentenone (II) and the lower aliphatic carboxylic acid or its metal or amine salt is usually performed at an elevated temperature in the presence or absence of a solvent. For the reaction, the lower aliphatic carboxylic acid and/or its metal or amine salt are/is normally employed in an amount of not less than 1.5 equivalents, preferably two or more equivalents, with respect to the 4-cyclopentenone (II). Although there is no particular restriction on the upper limit, the usual maximum limit is 30 equivalents.

As the solvent, there may be used any solvent that is inert to the reaction, and specific examples thereof are hydrocarbons (e.g. benzene, toluene), halogenated hydrocarbons (e.g. dichloromethane, dichloroethane, chloroform, carbon tetrachloride, chlorobenzene), ethers (e.g. tetrahydrofuran, dimethyl ether), ketones (e.g. acetone, methyl ethyl ketone), dimethylformamide, dimethylsulfoxide, etc. Mixtures of such solvents are also usable. Further, the lower aliphatic carboxylic acid employed as the reagent may itself be used as the reaction medium, when employed in excess.

The reaction temperature is usually from 30° to 160° C., preferably from 40° to 140° C. There is no particular limitation on the reaction time.

The recovery of the thus produced 2-cyclopentenone ester (I) wherein R₃CO— corresponds to the acyl moiety in the lower aliphatic carboxylic acid or its metal or amine salt as employed from the reaction mixture may be attained by per se conventional separation procedures such as extraction, fractionation, concentration, distillation, etc.

In the course of the reaction according to the process of the invention, racemization takes place simultaneously in the usual cases. Therefore, the use of the optically active 4-cyclopentenone (II) as the starting material gives the racemic 2-cyclopentenone ester (I). (Practically, the product may show slightly dextro- or levo-rotation, but the rotation is so slight that the product may be considered to be a racemate.) It happens frequently that only one optically active form of the 4-cyclopentenone (II) itself has a certain practical utility, for instance, as the intermediate in the production of agricultural chemicals, but its antipode does not have any practical utility. Said racemization is advantageous in making such useless antipode practically valuable.

Practical and presently preferred embodiments of the invention are illustratively shown in the following Examples.

EXAMPLE 1

Into a four necked flask equipped with an agitator and a thermometer, 3-acetoxy-2-allyl-3-methyl-4-cyclopentenone (19.4 g), acetic acid (80 ml) and sodium acetate (4 g) were charged and refluxed for 5 hours with agitation. After the completion of the reaction, acetic acid was evaporated off under reduced pressure. The residue was shaken with toluene (70 ml) and water (40 ml). The organic layer was separated, washed with an aqueous solution of sodium bicarbonate and then water and concentrated. The residue was distilled to obtain 4-acetoxy-2-allyl-3-methyl-2-cyclopentenone (16.7 g). Yield, 86%. B.P., 100°–110° C./0.1–0.3 mmHg.

In the same manner as above but using the acetate as shown in Table 1 in place of sodium acetate, the reaction was affected to obtain a desired product. The results are shown in Table 1.

TABLE 1

| Acetate (g) | Yield (%) |
|---|---|
| Copper acetate (4 g) | 92 |
| Sodium acetate (3 g) | 87 |
| Triethylamine acetate (1 g) | |
| Lead acetate (5 g) | 81 |
| Zinc acetate (5 g) | 80 |

EXAMPLES 2 TO 8

In the same manner as in Example 1 but using the 4-cyclopentenone as shown in Table 2 in place of 3-acetoxy-2-allyl-3-methyl-4-cyclopentenone, the reaction was effected to obtain a desired product. The results are shown in Table 2.

TABLE 2

| Example No. | 4-Cyclopentenone (II) | | | | 2-Cyclopentenone ester (I) | | |
|---|---|---|---|---|---|---|---|
| | R | $R_1$ | $R_2$ | Amount (g) | $R_3$ | Amount (g) | Yield (%) |
| 2 | $COCH_3$ | $CH_3$ | $n-C_5H_{11}$ | 22.4 | $CH_3$ | 20.3 | 91 |
| 3 | $COCH_3$ | $CH_3$ | $CH_2C{\equiv}CH$ | 19.2 | $CH_3$ | 15.9 | 83 |
| 4 | $COCH_3$ | $CH_3$ | $CH_3$ | 16.8 | $CH_3$ | 14.9 | 89 |
| 5 | $COCH_3$ | $CH_3$ | cis $CH_2CH{=}CHCH_2CH_3$ | 22.2 | $CH_3$ | 19.7 | 89 |
| 6 | $COCH_3$ | H | $n-C_5H_{11}$ | 21.0 | $CH_3$ | 19.9 | 95 |
| 7 | $COCH_3$ | H | cis $CH_2CH{=}CHCH_2CH_3$ | 20.8 | $CH_3$ | 19.5 | 94 |
| 8 | $COCH_3$ | H |  | 10 | $CH_3$ | 8.7 | 87 |

EXAMPLE 9

In the same apparatus as in Example 1, 3-acetoxy-2-allyl-3-methyl-4-cyclopentenone (19.4 g), propionic acid (70 ml) and sodium propionate (5 g) were charged and agitated at 110° to 120° C. for 6 hours. After the completion of the reaction, propionic acid was evaporated off under reduced pressure. The residue was extracted with toluene (70 ml) and water (40 ml) and treated as in Example 1 to obtain 2-allyl-4-propionyloxy-3-methyl-2-cyclopentenone (16.1 g). Yield, 83%. B.P., 115°–120° C./0.1–0.2 mmHg.

EXAMPLES 10 AND 11

In the same manner as in Example 9 but using the 4-cyclopentenone as shown in Table 3 in place of 3-acetoxy-2-allyl-3-methyl-4-cyclopentenone, the reaction was effected to obtain a desired product. The results are shown in Table 3.

TABLE 3

| Example No. | 4-Cyclopentenone (II) | | | | 2-Cyclopentenone ester (I) | | |
|---|---|---|---|---|---|---|---|
| | R | $R_1$ | $R_2$ | Amount (g) | $R_3$ | Amount (g) | Yield (%) |
| 10 | $COCH_3$ | $CH_3$ | $n-C_5H_{11}$ | 22.4 | $C_2H_5$ | 19.2 | 86 |
| 11 | $COCH_3$ | H | $n-C_5H_{11}$ | 21.0 | $C_2H_5$ | 18.9 | 90 |

EXAMPLE 12

In the same apparatus as in Example 1, 3-acetoxy-2-n-pentyl-3-methyl-4-cyclopentenone (22.4 g), toluene (60 ml), acetic acid (10 ml) and sodium acetate (4 g) were charged and heated for 10 hours with agitation. After the completion of the reaction, acetic acid was evaporated off under reduced pressure. The residue was extracted with toluene (70 ml) and water (50 ml) and treated as in Example 1 to obtain 4-acetoxy-2-n-pentyl-3-methyl-2-cyclopentenone (18.6 g). Yield, 83%, B.P., 125°–135° C./0.2–0.5 mmHg.

EXAMPLE 13

In the same apparatus as in Example 1, 2-allyl-3-hydroxy-3-methyl-4-cyclopentenone (15.2 g), acetic acid (45 ml) and sodium acetate (2 g) were charged and heated to reflux for 7 hours. After the completion of the reaction, acetic acid was evaporated off under reduced pressure. The residue was extracted with toluene (60 ml) and water (40 ml) and treated as in Example 1 to obtain 4-acetoxy-2-allyl-3-methyl-2-cyclopentenone (18.5 g). Yield, 95.3%. B.P., 100°–110° C./0.1–0.3 mmHg.

In the same manner as above but using the acetate as shown in Table 4 in place of sodium acetate, the reaction was effected to obtain a desired product. The results are shown in Table 4.

TABLE 4

| Acetate (g) | Yield (%) |
|---|---|
| Zinc acetate (5 g) | 93.6 |
| Copper acetate (4 g) | 92.8 |
| Sodium acetate (1 g) | 94.5 |
| Triethylamine acetate (1 g) | |
| Lead acetate (6 g) | 95.0 |
| Cobalt acetate (5 g) | 90.0 |

EXAMPLES 14 TO 21

In the same manner as in Example 13 but using the 4-cyclopentenone (II) as shown in Table 5 in place of 2-allyl-3-hydroxy-3-methyl-4-cyclopentenone, the reaction was effected. The results are shown in Table 5.

TABLE 5

| Example No. | 4-Cyclopentenone (II) | | | | 2-Cyclopentenone ester (I) | | | |
|---|---|---|---|---|---|---|---|---|
| | R | $R_1$ | $R_2$ | Amount (g) | $R_3$ | Yield (%) | Physical property (b.p.) | |
| 14 | H | $CH_3$ | $n-C_5H_{11}$ | 18.2 | $CH_3$ | 96.2 | 120–130° C./0.15–0.4 mmHg | |
| 15 | H | $CH_3$ | $CH_2C{\equiv}CH$ | 15.0 | $CH_3$ | 92.1 | 110–115° C./0.1–0.3 mmHg | |
| 16 | H | $CH_3$ | $CH_3$ | 12.6 | $CH_3$ | 95.5 | 105–115° C./1.5–2 mmHg | |
| 17 | H | $CH_3$ | cis $CH_2CH{=}CHCH_2CH_3$ | 18.0 | $CH_3$ | 94.6 | 130–135° C./0.5–1 mmHg | |
| 18 | H | H | $n-C_5H_{11}$ | 16.8 | $CH_3$ | 96.0 | 110–115° C./0.8–1 mmHg | |
| 19 | H | H | $n-C_6H_{13}$ | 18.2 | $CH_3$ | 95.5 | 120–125° C./1 mmHg | |
| 20 | H | H | cis $CH_2CH{=}CHCH_2CH_3$ | 16.6 | $CH_3$ | 94.3 | 115–120° C./1 mmHg | |
| 21 | H | H |  | 18.8 | $CH_3$ | 94.5 | 170–175° C./1 mmHg | |

EXAMPLE 22

In the same apparatus as in Example 1, 2-allyl-3-hydroxy-3-methyl-4-cyclopentenone (15.2 g), propionic acid (60 ml) and sodium propionate (3 g) were charged and heated at 120° to 130° C. for 8 hours with agitation. After the completion of the reaction, propionic acid was evaporated off under reduced pressure. The residue was extracted with toluene (60 ml) and water (40 ml) and treated as in Example 1 to obtain 2-allyl-4-propionyloxy-3-methyl-2-cyclopentenone (19.7 g). Yield, 94.7%. B.P., 115°-120° C./0.1-0.2 mmHg.

EXAMPLES 23 TO 25

In the same manner as in Example 22 but using the 4-cyclopentenone (II) as shown in Table 6 in place of 2-allyl-3-hydroxy-3-methyl-4-cyclopentenone, the reaction was effected to obtain a desired product. The results are shown in Table 6.

TABLE 6

| Example No. | 4-Cyclopentenone (II) | | | | 2-Cyclopentenone ester (I) | | |
|---|---|---|---|---|---|---|---|
| | R | $R_1$ | $R_2$ | Amount (g) | $R_3$ | Yield (%) | Physical property (b.p.) |
| 23 | H | $CH_3$ | n-$C_5H_{11}$ | 18.2 | $C_2H_5$ | 95.5 | 135-140° C./0.2-0.4 mmHg |
| 24 | H | H | n-$C_5H_{11}$ | 16.8 | $C_2H_5$ | 95.0 | 120-125° C./0.8-1 mmHg |
| 25 | H | $CH_3$ | cis $CH_2CH=CHCH_2CH_3$ | 18.0 | $C_2H_5$ | 94.6 | 140-145° C./0.5-1 mmHg |

EXAMPLE 26

In the same apparatus as in Example 1, 3-hydroxy-2-n-pentyl-3-methyl-4-cyclopentenone (18.2 g) and acetic acid (55 ml) were charged and heated under reflux for 15 hours with agitation. After the completion of the reaction, acetic acid was evaporated off under reduced pressure. The residue was extracted with toluene (80 ml) and water (50 ml) and treated as in Example 1 to obtain 2-n-pentyl-3-methyl-4-acetoxy-2-cyclopentenone (20.6 g). Yield, 92%. B.P., 125°-135° C./0.2-0.5 mmHg.

EXAMPLE 27

In the same apparatus as in Example 1, α-2-allyl-3-hydroxy-3-methyl-4-cyclopentenone (3.8 g, $[\alpha]_D^{20}+22.5°$ (c=1, chloroform)), acetic acid (20 ml) and sodium acetate (0.4 g) were charged and refluxed for 7 hours with agitation. After the completion of the reaction, acetic acid was evaporated off under reduced pressure. The residue was extracted with toluene (20 ml) and water (10 ml) and treated as in Example 1. Purification by the use of column chromatography gave 4-acetoxy-2-allyl-3-methyl-2-cyclopentenone (3.65 g). Yield, 94%. B.P., 100°-110° C./0.1-0.3 mmHg. $[\alpha]_D^{20}-1.8°$ (c=1, chloroform).

In the same manner as above but using the acetate as shown in Table 7 in place of sodium acetate, the reaction was effected. The results are shown in Table 7.

TABLE 7

| Acetate (g) | Product | |
|---|---|---|
| | Yield (%) | $[\alpha]_D^{20}$ |
| Copper acetate (1 g) | 91.5 | −1.2° |
| Sodium acetate (0.25 g) | 93.5 | −1.9° |
| Triethylamine acetate (0.25 g) | | |

EXAMPLE 28

In the same manner as in Example 27 but using l-2-allyl-3-hydroxy-3-methyl-4-cyclopentenone (3.8 g, $[\alpha]_D^{20}-23.9°$ (c=1, chloroform)) in place of d-2-allyl-3-hydroxy-3-methyl-4-cyclopentenone, the reaction was effected. The residue was treated as in Example 27 and purified by the use of column chromatography (eluent, toluene/ethyl acetate=10:1) to obtain 4-acetoxy-2-allyl-3-methyl-2-cyclopentenone (3.53 g). Yield, 91%. $[\alpha]_D^{20}+2.4°$ (c=1, chloroform).

EXAMPLE 29

In the same apparatus as in Example 1, l-3-acetoxy-2-allyl-3-methyl-4-cyclopentenone (3.88 g, $[\alpha]_D^{20}-9.36°$ (c=1, chloroform)), propionic acid (30 ml) and sodium propionate (1.5 g) were charged and heated at 110° to 120° C. for 6 hours with agitation. After the completion of the reaction, propionic acid was evaporated off under reduced pressure. The residue was extracted with toluene (30 ml) and water (20 ml) and treated as in Example 28 to obtain 2-allyl-4-propionyloxy-3-methyl-2-cyclopentenone (3.1 g). Yield, 80%. B.P., 100°-110° C./0.1-0.3 mmHg. $[\alpha]_D^{20}-1.1°$ (c=1, chloroform).

EXAMPLE 30

In the same apparatus as in Example 1, l-3-acetoxy-2-allyl-3-methyl-4-cyclopentenone (3.88 g, $[\alpha]_D^{20}-93.6°$ (c=1, chloroform)), acetic acid (30 ml) and sodium acetate (1 g) were charged and refluxed for 5 hours with agitation. After the completion of the reaction, acetic acid was evaporated off under reduced pressure. The residue was extracted with toluene (30 ml) and water (20 ml). The organic layer was separated, washed with an aqueous solution of sodium bicarbonate, and concentrated. Purification by the use of column chromatography gave 4-acetoxy-2allyl-3-methyl-2-cyclopentenone (3.18 g). Yield, 82%. $[\alpha]_D^{20}-0.9°$ (c=1, chloroform).

EXAMPLES 31 TO 35

In the same manner as in Example 30 but using the optically active 4-cyclopentenone (II) as shown in Table 8, the reaction was effected. The results are shown in Table 8.

TABLE 8

| Example No. | 4-Cyclopentenone (II) | | | | | 2-Cyclopentenone ester (I) | | | |
|---|---|---|---|---|---|---|---|---|---|
| | R | $R_1$ | $R_2$ | $[\alpha]_D^{20}$ | Amount (g) | $R_3$ | Amount (g) | Yield (%) | $[\alpha]_D^{20}$ |
| 31 | $COCH_3$ | $CH_3$ | n-$C_5H_{11}$ | −69.4° | 4.48 | $CH_3$ | 3.99 | 89 | −0.9° |
| 32 | $COCH_3$ | $CH_3$ | $CH_2C\equiv CH$ | −16.2° | 3.84 | $CH_3$ | 3.11 | 81 | −1.4° |
| 33 | $COCH_3$ | $CH_3$ | $CH_2CH_2CH=CH_2$ | −84.6° | 4.16 | $CH_3$ | 3.54 | 85 | −1.0° |
| 34 | $COCH_3$ | H | n-$C_5H_{11}$ | +112.0° | 4.2 | $CH_3$ | 3.91 | 93 | +4° |

TABLE 8-continued

| Example No. | 4-Cyclopentenone (II) | | | | | 2-Cyclopentenone ester (I) | | | |
|---|---|---|---|---|---|---|---|---|---|
| | R | $R_1$ | $R_2$ | $[\alpha]_D^{20}$ | Amount (g) | $R_3$ | Amount (g) | Yield (%) | $[\alpha]_D^{20}$ |
| 35 | $COCH_3$ | H | $CH_2CH=CH_2$ | +68.8° | 3.6 | $CH_3$ | 3.29 | 91.5 | +7° |

EXAMPLES 36 TO 40

In the same manner as in Example 27 but using the optically active 4-cyclopentenone (II) as shown in Table 9, the reaction was effected. The results are shown in Table 9.

TABLE 9

| Example No. | 4-Cyclopentenone (II) | | | | | 2-Cyclopentenone ester (I) | | | |
|---|---|---|---|---|---|---|---|---|---|
| | R | $R_1$ | $R_2$ | $[\alpha]_D^{20}$ | Amount (g) | $R_3$ | Amount (g) | Yield (%) | $[\alpha]_D^{20}$ |
| 36 | H | $CH_3$ | $n$-$C_5H_{11}$ | +17.5° | 3.64 | $CH_3$ | 4.19 | 95.3 | −2.5° |
| 37 | H | $CH_3$ | $CH_2C\equiv CH$ | −131.7° | 3.0 | $CH_3$ | 3.45 | 90 | +2.1° |
| 38 | H | $CH_3$ | $CH_3$ | −24.3° | 2.52 | $CH_3$ | 3.11 | 92.5 | +1.8° |
| 39 | H | H | $n$-$C_5H_{11}$ | −53.3° | 3.36 | $CH_3$ | 3.97 | 94.5 | +4.2° |
| 40 | H | H | $CH_2CH=CH_2$ | −28.2° | 2.8 | $CH_3$ | 3.38 | 94 | +8.1° |

EXAMPLE 41

In the same apparatus as in Example 1, propionic acid (20 ml) and sodium propionate (1.5 g) were charged and heated to 100° C. Then, 1-3-acetoxy-2,3-dimethyl-4-cyclopentenone (3.36 g, $[\alpha]_D^{20}$ −19.6° (c=1, chloroform)) was dropwise added thereto over 1 hour. After the completion of the reaction, the reaction mixture was treated as in Example 29 to obtain 2,3-dimethyl-4-propionyloxy-2-cyclopentenone (3.02 g). Yield, 83%. $[\alpha]_D^{20}$ −0.6° (c=1, chloroform).

COMPARATIVE EXAMPLE 1

3-Acetoxy-2-allyl-3-methyl-4-cyclopentenone (3.9 g) was adsorbed on a column of neutral alumina (100 g). After 1 hour, the column was eluted with a mixture of benzene and ethyl ether (95:5 by volume). The eluate was concentrated to obtain 4-acetoxy-2-allyl-3-methyl-2-cyclopentenone in a yield of 25%.

What is claimed is:

1. A process for preparing 2-cyclopentenone esters of the formula:

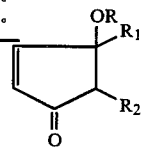

(I)

wherein $R^1$ is hydrogen, lower alkyl or lower alkenyl, $R^2$ is lower alkyl, lower alkenyl, lower alkynyl, cycloalkyl, cycloalkenyl or substituted or unsubstituted aryl and $R^3$ is hydrogen or lower alkyl, which comprises reacting a racemic or optically active 4-cyclopentenone of the formula:

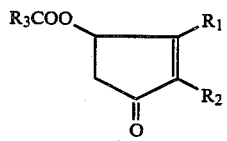

(II)

wherein $R^1$ and $R^2$ are each defined above and R is hydrogen or acyl with at least one lower aliphatic carboxylic acid and/or a metal or amine salt thereof.

2. The process according to claim 1, wherein at least one lower aliphatic carboxylic acid and at least one metal or amine salt thereof are used in combination.

3. The process according to claim 1, wherein the lower aliphatic carboxylic acid is formic acid, acetic acid, propionic acid, butyric acid or valeric acid.

4. The process according to claim 1, wherein the metal salt of the lower aliphatic carboxylic acid is selected from the group consisting of the lithium, sodium, potassium, calcium, copper, zinc, palladium, lead, tin and manganese salt thereof.

5. The process according to claim 1, wherein the amine salt of the lower aliphatic carboxylic acid is selected from the group consisting of the trimethylamine, triethylamine, pyridine and picolic acid salts thereof.

6. The process according to claim 1, wherein the reaction temperature is from 30° to 160° C.

7. The process according to claim 2, wherein the lower aliphatic carboxylic acid is formic acid, acetic acid, propionic acid, butyric acid or valeric acid.

8. The process according to claim 2, wherein the metal salt of the lower aliphatic carboxylic acid is selected from the group consisting of the lithium, sodium, potassium, calcium, copper, zinc, palladium, lead, tin and manganese salts thereof.

9. The process according to claim 2, wherein the amine salt of the lower aliphatic carboxylic acid is selected from the group consisting of the trimethylamine, triethylamine, pyridine and picolic acid salts thereof.

* * * * *